United States Patent [19]

Katims

[11] Patent Number: 4,503,863

[45] Date of Patent: * Mar. 12, 1985

[54] METHOD AND APPARATUS FOR TRANSCUTANEOUS ELECTRICAL STIMULATION

[76] Inventor: Jefferson J. Katims, 5813 Greenspring Ave., Baltimore, Md. 21209

[*] Notice: The portion of the term of this patent subsequent to Dec. 15, 1998 has been disclaimed.

[21] Appl. No.: 302,340

[22] Filed: Sep. 15, 1981

Related U.S. Application Data

[63] Continuation-in-part of Ser. No. 53,568, Jun. 29, 1979, Pat. No. 4,305,402.

[51] Int. Cl.³ ............... A61B 5/05; A61N 1/32
[52] U.S. Cl. .................. 128/741; 128/1 C; 128/732; 128/421; 128/905
[58] Field of Search .............. 128/1 C, 731–734, 128/741, 419 R, 420 R, 421, 422, 423 R, 905, 128/791–793

[56] References Cited

U.S. PATENT DOCUMENTS

| | | | |
|---|---|---|---|
| 1,257,555 | 2/1918 | Vreeland | 128/422 |
| 3,032,029 | 5/1962 | Cunningham | 128/733 |
| 3,255,753 | 6/1966 | Wing | 128/1 C |
| 3,464,416 | 9/1969 | Williams | 128/421 |
| 3,495,596 | 2/1970 | Condict | 128/1 C |
| 3,640,284 | 2/1972 | DeLangis | 128/422 |
| 3,659,614 | 5/1972 | Jankelson | 128/791 |
| 3,791,373 | 2/1974 | Winkler et al. | 128/1 C |
| 3,817,254 | 6/1974 | Maurer | 128/421 |
| 3,835,833 | 9/1974 | Limoge | 128/1 C |
| 3,881,495 | 5/1975 | Penozzo et al. | 128/422 |
| 3,886,931 | 6/1975 | Rodler | 128/741 |
| 3,893,450 | 7/1975 | Ertl | 128/731 |
| 3,951,134 | 4/1976 | McLech | 128/731 X |
| 3,967,616 | 7/1976 | Ross | 128/1 C |
| 3,971,365 | 7/1976 | Smith | 128/734 |
| 4,094,307 | 6/1978 | Young, Jr. | 128/731 |
| 4,121,593 | 10/1978 | Kestrubin et al. | 128/1 C X |

FOREIGN PATENT DOCUMENTS

635994  12/1978  U.S.S.R. .................. 128/419 R

Primary Examiner—Lee S. Cohen
Attorney, Agent, or Firm—Karl W. Flocks; Sheridan Neimark; A. Fred Starobin

[57] ABSTRACT

A method and apparatus for monitoring and obtaining actual bio-electrical characteristics of a subject under predetermined conditions of evoked response stimuli, and by interaction with a computer, applying cutaneous electrical stimulation to the subject, using a signal generator to modify current amplitude and frequency in a direction to achieve bio-electrical characteristics in the subject related to the actual bio-electrical characteristics monitored. The signal generator uses a sinusoidal waveform output, with battery power passed through a transformer to power a transconductance amplifier to obtain constant current output despite resistance changes in the line with the subject, and with the transformer not placed in the signal path of the sinusoidal waveform. The signal may be obtained from a sinusoidal oscillator of wide frequency having switched integrator sections connected to an inverting amplifier, pulse generator and gating.

27 Claims, 10 Drawing Figures

METHOD AND APPARATUS FOR TRANSCUTANEOUS ELECTRICAL STIMULATION

BACKGROUND OF THE INVENTION

This application is a continuation-in-part of Ser. No. 053,568, filed 6/29/79, now U.S. Pat. No. 4,305,402 of Jefferson Jacob Katims, issued Dec. 15, 1981, and entitled "METHOD AND APPARATUS FOR TRANSCUTANEOUS ELECTRICAL STIMULATION".

The present invention relates to bio-electric stimulators and more particularly to stimulation by transcutaneous application of electricity as a therapeutic tool.

In medicine the earliest known bio-electric stimulators utilized for the direct application of electricity to the human skin as a therapeutic tool appeared around 1750. The direct application of electrical stimulation to human neuronal tissue or stimulation has also been in a therapeutic use for the past 20 years.

Various therapeutic applications of mild electric stimulation, in contrast to gross stimulation such as electroconvulsive shock, directly applied to human skin has been purported to include sleep induction or curing of insomnia, anesthesia, analgesia, attenuation of withdrawal from drug addiction, relief from asthma, as well as relief from anxiety and depression.

The therapeutic applications of direct electrical stimulation to neural tissue or subcutaneous stimulation includes induction of analgesia, alleviation of symptoms of multiple sclerosis, cerebral palsy, epilepsy and spasticity, facilitation of the healing of non-union bone fractures, cardiac and diaphragm pacemakers, as well as electrical bladder control. Another application of electrical stimulation is in the field of bio-research, primarily electrophysiology.

A widely used diagnostic device used today in modern medical neurology is the pin. The neurologist routinely employs the pin to scratch or prick a patient's skin to test the integrity of the nerve fibers which innervate the cutaneous area being stimulated. This type of diagnostic procedure provides critical information as to whether a nerve fiber has been damaged by, for example, an industrial toxic agent such as acrylate. There are many serious drawbacks to this diagnostic procedure, including the following:

It is impossible to apply the pin to the skin with an equal pressure to all skin regions being treated. This makes it difficult for the neurologist to get a clear understanding of the patient's response.

This diagnostic procedure is not quantitative.

The pin can puncture or scratch the tissues being stimulated.

Among the first nerve fibers to be damaged by acrylate are those which innervate the toes. Due to the fact that several regions of the toes and feet are often unevenly caloused, it is difficult for a neurologist to get a clear picture of possible nerve damage in this area by the use of a pin.

SUMMARY OF THE INVENTION

It is an object of the present invention to be able to provide a unique medical record of the brain's electrophysiological state and its response to different frequencies and types of stimulation which is of great value in the field of neurology. The present invention can also be utilized for the study of intelligence and psychoneurological disorders.

Eventually, a doctor, after completing a profile on a patient, utilizing the present invention, would be able to prescribe machine settings in order to help the patient wake up, go to sleep, replace drugs, play a song, or a game of pinball.

A further advantage of the present invention is its use in the electrical stimulator of a constant current output. The advantage of a constant current output is that it automatically accounts and corrects for any fluctuations in electrical resistance that may occur within the overall system. This would not be accounted for by a constant voltage output. Constant current also provides a superior margin of electrical safety in comparison with constant voltage where fluctuations in electrical resistance can cause shocking to the subject. Changes in resistance could be due to natural endogenous fluctuations in the resistance of human tissue; i.e. perspiration, or exogenous resistance fluctuations caused by the drying out of electrode paste used with the electrodes.

Another advantage is use of constant current which resembles the natural current flow in neuroelectrophysiology. Caution must be exercised if a constant voltage source is applied instead of constant current since a person could serve as a rectifying load thereby leaving a net charge on their self which would lead to desensitization.

An additional safety feature of the present invention is a clipping system used in the electrical stimulator.

It is a further object of the present invention to establish a system for back and forth interaction between an electrical stimulator and a control computer.

Another object of the present invention is to disclose a method and apparatus which operates in response to an actual psycho-electrophysiological state to modify current amplitude and frequency in a direction to achieve the desired such state. In a more limited aspect, in response to an actual EEG, to modify amplitude of current and frequency in a direction to achieve a desired EEG.

Further, it is an object to achieve such state by cutaneous electrical stimulation.

Also it is an object to obtain therapy for the subject by producing altered subjective electrophysiological states in the subject. Value of the present invention is shown in the relief of subjective physiological distress associated with disease as well as creating a favorable subjective physiological state in the normal subject.

Also, it is a further object of this invention to avoid the problems associated with the diagnostic procedue which employs a pin. These problems can be avoided by the application of cutaneous electrical stimulation for the following reasons:

The pressure with which the cutaneous electrical stimulation is administered is not a factor of its diagnostic efficacy. What is being measured with cutaneous electrical stimulation is the threshold of the current intensity required to evoke a tingling sensation at the electrode site. The pressure with which the electrodes touch the skin does not affect the current threshold.

This cutaneous electrical stimulation diagnostic procedure is quantitative in that the current threshold value numbers can be recorded in the medical record and used for future comparison.

A further advantage of this technique is its neuronal frequency specificity. At different frequencies of stimulation different nerve fibers are stimulated which have different current thresholds for the cutaneous tingling sensation. This cutaneous electrical stimulation procedure has the advantage of providing the neurologist with the cutaneous threshold values for several different nerve populations at the same cutaneous location by the application of various frequencies, thus providing more information than the solitary non-quantitative cutaneous threshold obtained with a pin.

The cutaneous electrical stimulation diagnostic technique is not dangerous to the tissues being stimulated.

The cutaneous electrical stimulation diagnostic technique is not affected by calouses at the cutaneous sites being stimulated.

BRIEF DESCRIPTION OF THE DRAWING

The invention can best be understood by referring to the accompanying drawings in which.

DESCRIPTION OF THE PREFERRED EMBODIMENTS

First the theoretical basis of the present invention is discussed in terms of its output wave shape, frequency coding and physiology, as well as human neuroanatomy, neurochemistry, and neuropsychology.

A sinusoidal wave shape is the choice for use in the present invention based upon the desire to minimize the amplitude of the stimulating current and the observation by the present inventor that a sinusoidal wave shape is approximately 15 times more effective than a square wave in affecting the physiologial state of mammalian neuronal tissue. 1 pilot study performed in conjunction with studies for the present invention showed unpleasant subjective side effects for a square wave form and none such side effects for a sinusoidal wave form. A further convenience of the sinusoid is its simple frequency domain representation.

The frequency coding of individual neurons for both communication and in response to electrical stimulation, as well as the ability to induce electrocortical activity; e.g., recruitment of EEG, are well established facts in neuroscience. The frequency coding phenomenon may have to do with the temporal summation of the excitatory effect of a neurotransmitter at the synapse between neurons, or endogenous electrical time constants of neuronal membrances which are independent of neurotransmitters. It is the intent of the electrical stimulator in the present invention to try to excite endogenous rhythms within the brain as well as to stimulate particular brain regions to produce a psychotherapeutic affect. The frequency coding properties of a human's brain subjective psychological states in response to cutaneous application of this stimulator are demonstratable by experiments of the present invention.

By placing two electrodes on a human subject's skin over the jawbone in front of each earlobe and passing a current between them, there is created an electron flow of which approximately 95% passes through the face and 5% passes through the cranium. This 5% has been demonstrated to be capable of inducing slight fluctuations in brain electrical potentials for the duration of the stimulation in humans. These fluctuations could account for one of the ways in which the machine used in the present invention could induce electrocortical activity; the other possible type of electrocortical induction is discussed later in dealing with the nucleus of the reticular formation.

The 95% of the current flow passing through the face is capable of directly inducing fluctuations in the resting membrane potentials of the nerve fibers innervating the face and the entire underlying musculature. The sensory and motor fibers being stimulated primarily involve the fifth (V) cranial nerve, the trigeminal. Other cranial nerve fibers are stimulated as well including nerves VII, X, XI and XII. The primary locus of the theoretical basis of the mechanism of action of the machine in the present invention concerns the trigeninal nerve. The cell bodies of its primary sensory fibers are located deep within the midbrain in the trigeminal nucleus. These cell bodies are the only unencapsulated primary sensory neurons within the central nervous system. It is the intent of the stimulator of the present invention, by the method of the present invention, to selectively stimulate these neurons with different frequencies of electrical stimulation, in effect to affect their activity and the activity of associated neurons in other brain stem nuclei. Through this process one is able to induce neuroelectrical and endogenous neurochemical changes in the human brain state.

Stimulation of the trigeminal nucleus and its sensory fibers as well as classical acupuncture has been demonstrated to be capable of inducing electrocortical activity. Both the putative neurotransmitters, Substance P and Enkephalin, have been found in neurons within this nucleus. Both of these putative neurotransmitters have been postulated to be involved with limbic emotional brain functions. It should be mentioned here that the Enkaphalins have been demonstrated to be our own endogenous opiate-like substance. Both the antidepressants and the tranquilizers are drugs which exert an influence on this nucleus with the brain.

The following brain stem nuclei mentioned all have intimate neuronal connections with the trigeminal nucleus.

The nucleus ambiguus contains some of the cell bodies of cranial nerves IX, X and IX. The auricular branch of the vagus nerve (X) enters the trigeminal nucleus from the nucleus ambiguus. The fibers from the vagus nerve (X) provide primary central sensory and motor innervations of the heart, lungs, and the gastrointestinal tract.

The primary role of the nucleus of the reticular formation is in the regulation of all types of electrocortical activity.

The portion of the reticular formation comprising the nucleus gigantocellularis within the pontine tegmentum has been found to be essential for dreaming to occur. The nucleus gigantocellularis has also been demonstrated to have intimate neurochemical associations with the trigeminal nucleus.

The central gray region contains among the densest concentration of Enkephalins within the brain; if stimulated electrically it will induce analgesia in humans.

The neurons within the raphae nuclei utilize the neurotransmitter serotonin which is involved in the fundamental regulation of the sleep-wakefulness cycle and is a system which is affected by psychedelic drugs.

The locus coeruleui, blue in their natural state within the brain, contain cell bodies which are adjacent to cell bodies of the trigeminal nucleus. This close anatomical relationship would facilitate an electrotonic interaction between these two groups of cell bodies. The locus coeruleus is one of the primary sources of the noradrenergic neurotransmitter system within the human brain. This system is involved with learning and memory, depression and pleasure, and certain psychotic disorders. It is affected by drugs such as cocaine and heroin.

The vestibular nucleus is involved with our sense of balance as well as nausea.

The inferior and superior colliculi are associated with a primitive body, space, auditory, and visual sense system.

The cerebellum portion of our brain represent a primitive motor cortex and plays a role in complex timing functions, learning and memory, and execution of complex motor tasks.

The present invention is concerned with the above theoretical basis but it is from investigations by the inventor that the method and apparatus of the invention has evolved.

Figure 1:
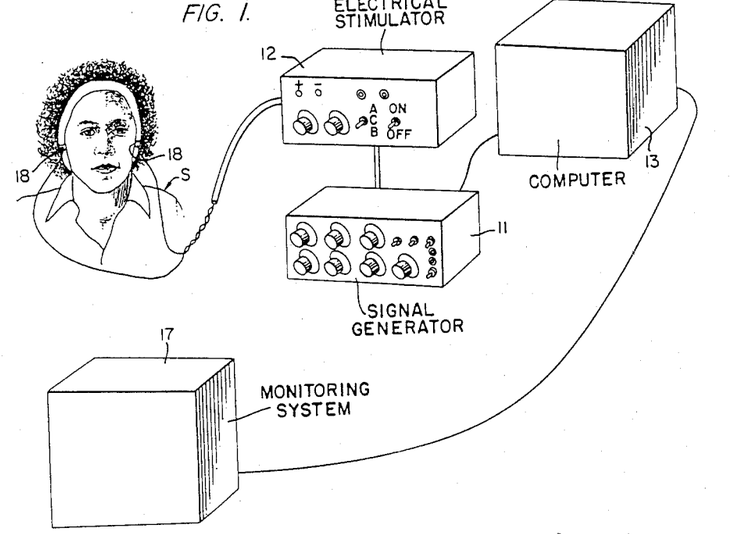
FIG. 1 is an illustration of the system of the present invention connected to a subject.
Figure 2:
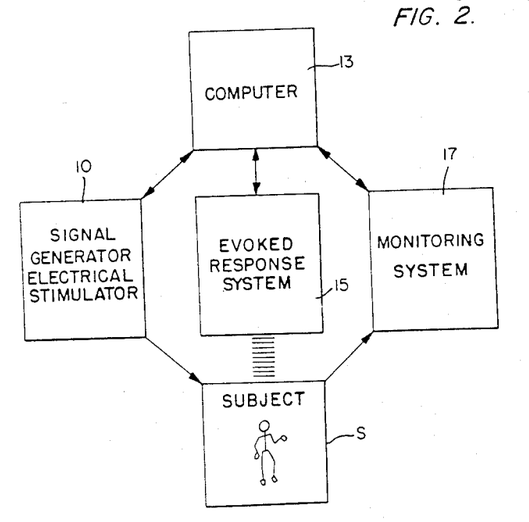
FIG. 2 is a block diagram illustration of the overall system.

FIGS. 1 and 2 show the over-all system. The signal generator electrical apparatus 10 is composed of a triple output signal generator 11 and electrical stimulator 12 interfaced to be under control of computer 13. Although signal generator 11 and electrical stimulator 12 are shown in the illustrated embodiment of FIGS. 1 and 2; as many generators as necessary may be utilized or electrical stimulator 12 may be used alone. Outputs from apparatus 10 go to the subject S and to computer 13.

Evoked response system 15 may be any audio, visual, tactile, or situational stimuli whatsoever and this system is also interfaced with computer 13.

Examples of evoked-response stimuli are:

1. Audio stimuli such as any good commercial music synthesizer which can be interfaced to computer 13. A well interfaced and controlled sound reproduction system is also desired.

2. Visual stimuli such as any standard video camera and monitor system in closed circuit television. A video synthesizer would also be included in this system.

3. Tactile stimuli which could include such things as a solenoid or piezoelectric activated skin stimulator, an electrical vibrator, such as the type used for massage, or bone conduction hearing aids.

4. Psychological stimuli which concern the conditions under which the subject is being treated. This could be programmed into computer 13.

Monitoring system 17 which is also interfaced with computer 13 and receives outputs from subjects, is composed of three sub-systems (not shown). These sub-systems are:

1. A transducer system which receives inputs from any electrophysiological parameter which may be monitored from the subject; e.g., electrocardiogram (EKG), electromyelogram (EMG), galvanized skin resistance (GSR), electro-oculogram (EOG), blood pressure, breathing, etc. This system also utilizes a video camera, microphone, or electric light pencil as a type of input.

2. A preprocessing signal conditioning system which receives input from the transducer system and is interfaced such that it may be computer-controlled. This serves to provide a usable signal for the computer 13 and signal analysis (see following) systems. This system sends outputs to computer 13 and the signal analysis system. This system consists of preamplifiers, amplifiers, band pass amplifiers, etc.

3. A signal analysis system to perform real time analysis of the incoming data for the controlling computer 13. Examples of types of signal analysis performed include statistical temporal correlation, photo accoustic spectroscopy, EEG filtering techniques, Fourier analysis, and other forms of linear and non-linear signal analysis. Many components of this system could be incorporated into computer 13.

Monitoring here is done at the subject leads instead of at the primary side of the transformer in order to better account for variable impedances at the subject such as at the electrodes.

Computer 13 is a high-speed digital type of computer, capable of performing statistical correlative analysis and possessing a large amount of memory circuitry. Computer 13 is fully interfaced with the signal generator electrical system 10, the evoked response system 15, the preprocessing signal conditioning system and the signal analysis system, both described above as parts of monitoring system 17.

The function of computer 13 is to interactively simulate the subject S with the signal generating system 10 and the evoked response system 15 and monitor and analyze the data from the monitoring system 17 to induce a particular electrical or subjective state.

Computer 13 analyzes the EEG from output obtained via the signal analysis system in terms of evoked potentials, event-related potentials, pre- or post-stimulus potentials of an extremely long or short duration, habituation or dishabituation of evoked response, synchronization of output, fluctuations in negative or positive pre- or post-stimulus potentials, and recruitment of EEG frequencies with respect to frequencies of stimulation. Computer 13 is then programmed to correlate the EEG analysis data with the chemical, physiological and psychological state of the subject S.

The chemical state refers to whether the subject is under the influence or addicted to any drugs. the physiological state refers to any electrophysiological parameters being monitored by the computer. The psychological state refers to the subjective or objective psychological state and the state of attention of the subject, as well as psychological profiles of, say, a movie being observed (e.g., male vs. female characters) or performance in a pinball game (e.g., a hit vs. a miss).

Computer 13 will continually interface or mediate a two-way interaction between the subject's psychoelectrophysiological state and the stimuli to which the subject is being exposed or with which the subject is interacting. This application of computer 13 can be under control of either the subject or the observer.

For example, computer 13 can be programmed to automatically be able to compare and contrast different combinations and permutations of different frequencies of cutaneous electrical stimulation to determine which has the most efficient output in evoking the recruitment of synchronization of EEG activity. The latter is associated with a pleasurable or sedated state of consciousness. Computer 13 may modulate the evoked response system 15 as well, to achieve the same effect.

By comparing the components of electrocortical pre-post stimulus potentials evoked response and utilizing amplitude discrimination and monitoring the sequential frequency over time, computer 13 is able to modulate cutaneous current levels and frequencies utilizing the signal generator electrical stimulator system to prevent habituation or desenitization of the subject's electrophysiological state. This is a method by which computer 13 quantitatively maintains tingling subjective levels of electrical current.

Biofeedback parameters such as blood pressure, electrocardiogram, or breathing, which are monitored by the transducer system of monitoring system 17, may be analyzed by computer 13 and can be systematically correlated with the frequency dimension of the cutaneous electrical stimulation. Computer 13 can systematically evoke different frequencies of cutaneous stimulation to modulate cardiovascular or pulmonary rates to desired therapeutic levels.

For example, in therapeutic applications, while listening to a song, certain notes or patterns in the rhythm are correlated by computer 13 with the subject's electrophysiological state. Computer 13 can either accentuate the stimulus (in this case by affecting either the volume or timing of the music through the evoked response system 15), or the brain's electrical state (utilizing signal generator electrical stimulator system 10), or both in order to heighten the subject's awareness of both. This same logic may be applied towards a game of pinball, or a movie, any type of stimulus which may be applied therapeutically, or to maintain a high state of attentiveness in a subject for performance of a complex task.

Signal generator 11 is shown as connected to computer 13 and is a triple output signal generator used to send a large range of frequencies and combinations of these frequencies, through electrical stimulator 12 to a pair of electrodes 18 placed on the skin of subject's approximately ¼ inch anterior to each earlobe. The electrodes 18 may be dime electrodes, made in size, shape, and material similar to that coin. Although signal generator 11 is illustrated here, it is possible to practice the present invention with only electrical stimulator 12 of signal generator electrical stimulator apparatus 10, but at a sacrifice in general useful range. As illustrated in the enlarged view of its front panel in FIG. 3 and one portion of the block-schematic diagram of FIG. 5, signal generator 11 is composed of three waveform generators 21A, 21B, 21C, each with its frequency control 22A, 22B and 22C, respectively and its bandswitch control 23A, 23B and 23C, respectively. Power is supplied to the waveform generators 21A, 21B, 21C through power charge switch 24 from two 6-volt batteries connected in series for a 12-volt power supply (rechargeable as two 6-volt batteries in parallel). A battery low indicator 25 shown here as a light which indicates a need to recharge batteries is connected to power charge switch 24. Current output controls 26A, 26B, 26C from each of the waveform generators 21A, 21B, 21C, respectively, are illustrated as potentiometers 26A', 26B', 26C' and are connected to output terminal 29 through inverting amplifier 27 and master current control 28, noted as potentiometer 28'. A power switch and power-on indicator light are also shown for their normal purposes. All ground connections for signal generator 11 and electrical stimulator 12 are connected as a common ground.

Figure 6:
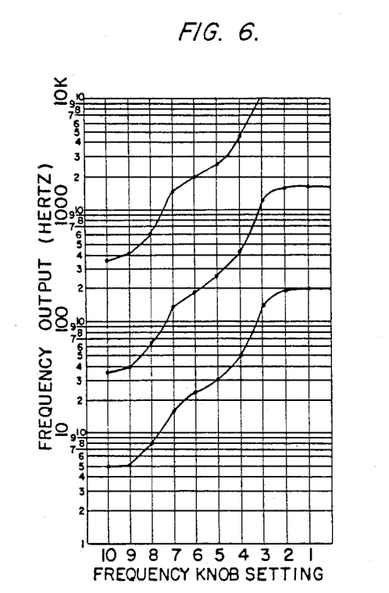
FIG. 6 is a graph showing frequency outputs for the knob settings of the signal generator of FIG. 3.

Each of the frequency bandswitch controls 23A, 23B, 23C have bandswitch positions A, B, and C designated with A designating the low frequency band, B designating a medium frequency band, and C designating a high frequency band. The frequency output for the knob settings on each of frequency controls 22A, 22B, 22C in each of the three bands A, B, and C is shown on the graph of FIG. 6. The three curves thereon designate the frequency in hertz for the knob settings on the particular signal generator used but this can be worked out for other signal generators which preferably will operate in the same ranges. For the particular signal generator used, the master control 28 regulated the over-all current output with a 10 mA maximum output current from amplifier 27. Each of waveform generators 21A, 21B, 21C in the preamplifier had a 1.3 V peak signal. This signal generator's amplifier had a 10 mA/V transfer function with the amplifier's level control at the full clockwise position.

Figure 3:
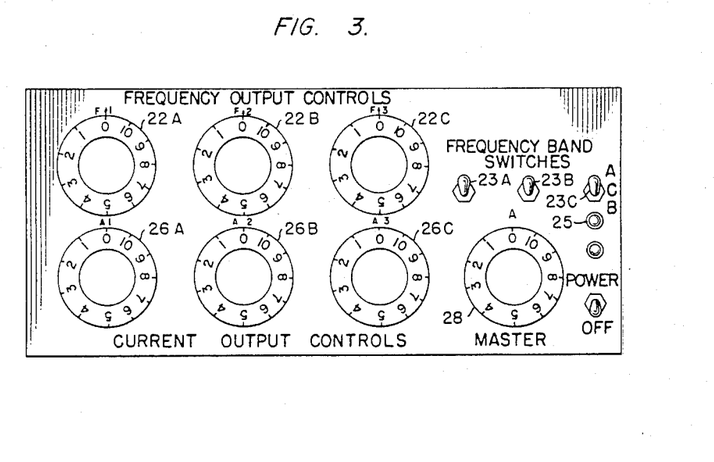
FIG. 3 is an enlarged view of the front panel of a signal generator used in the system.

The amplitude controls on the signal generator were calibrated within 5%. The individual level controls may be viewed as weighing factors and the master control as an over-all multiplier. The signals add in quadrature, i.e.:

$$\text{Peak output voltage } (V) = A_0(A_1^2 + A_2^2 + A_3^2)^{\frac{1}{2}}(1.3)$$

where $A_0$ is the setting of the master level control.

$A_1$, $A_2$, and $A_3$ are the settings of the individual level controls.

1.3 V is the peak output of the device.

It should be noted that the controls as illustrated read ten times the actual level (i.e., 0 to 10 instead of 0 to 1).

The particular signal generator specifications are to clearly illustrate a working embodiment but should not be construed as absolute limits since other signal generators that can be operated in these frequency ranges with similar output waveforms, particularly sinusoidal waveforms, can be used. Also the use of a triple output signal generator illustrated allows a wider range of results but the output of simulator 12 alone is sufficient for some more limited purposes.

Figure 5:
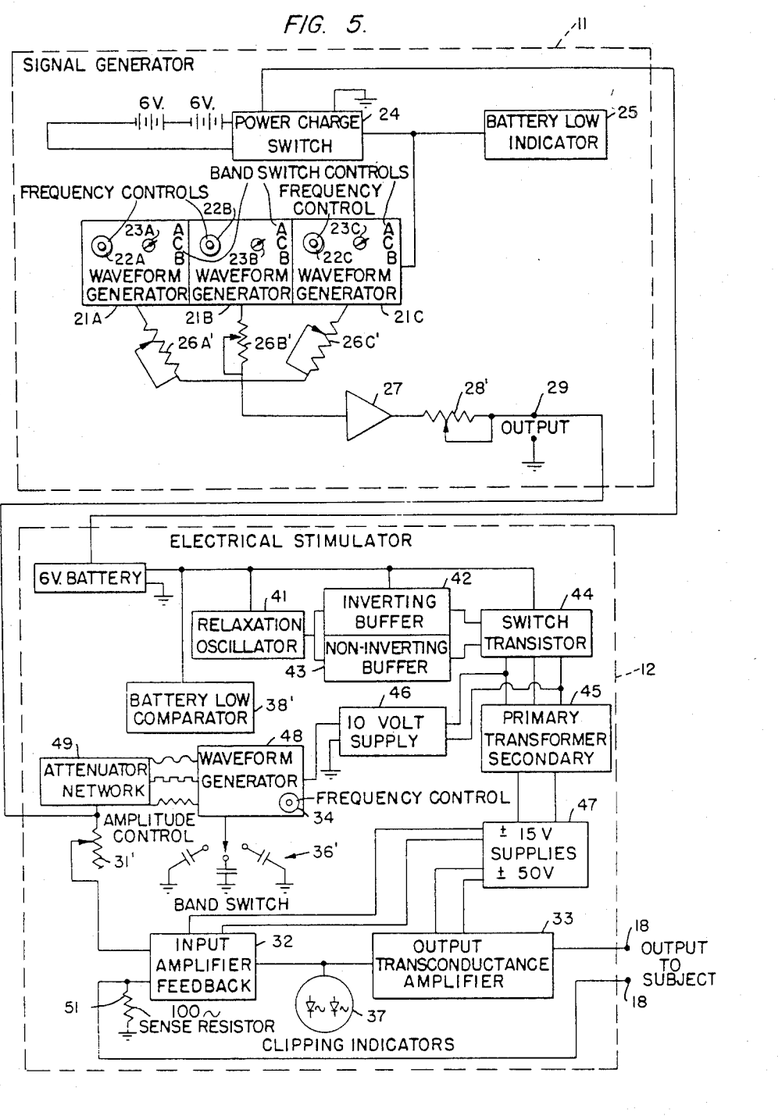
FIG. 5 is a block-schematic diagram of the signal generator and electrical stimulator of FIGS. 3 and 4, respectively.

Signal generator output terminal 29 is connected to electrical stimulator 12 as shown in FIG. 5, mainly utilizing amplifier characteristics of electrical stimulator 12 by passing the signal from terminal 29 through current amplitude control potentiometer 31', input amplifier 32, and output transconductance amplifier 33 to electrodes 18 contacting the subject S. Transconductance amplifier 33 maintains the constant current output despite fluctuations in the load.

Figure 4:
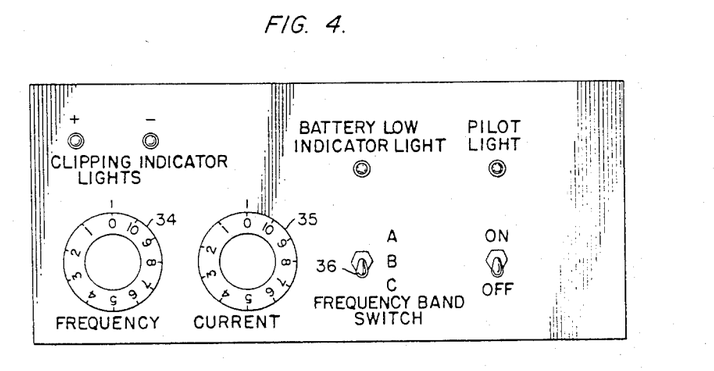
FIG. 4 is an enlarged view of the front panel of the electrical stimulator used in the system.

Referring to FIG. 4, the front panel of electrical stimulator 12 has a frequency control 34, current output control 35, frequency band switch 36, with clipping indicator lights 37, battery low indicator light 38 and a pilot light with the on-off switch with capabilities of a single output instead of the triple output of signal generator 11.

Referring to the block-schematic of FIG. 5, electrical stimulator 12 has a 6-volt battery supply. To this is connected battery low comparator 38', used in conjunction with a diode reference (not shown), and relaxation oscillator 41. Most any DC input can be used but the battery connection illustrated is preferred. From relaxation oscillator 41 a square wave output is buffered by inverting buffer 42, and non-inverting buffer 43 with their complementary outputs driving a pair of power transistors 44 which chop the 6-volt battery voltage at a rate of several kilohertz and drive step-up transformer 45. The induced voltage in the primary is full wave rectified to provide +10 volt supply 46. The secondary drives a full wave doubler circuit that provides ±50 volt supply 47.

Transformer 45 is used to match a high impedance load (the subject) and simple, safe, low-voltage circuitry without having the transformer in the signal path. In other machines of the type for electrical stimulation that use transformers, the fact that the transformer is in the signal path implies that all sorts of distortions that are inherent to the transformer such as frequency limiting effects and the fact that no DC current may pass through a transformer will interfere with the signal output from these other simulators.

In the machine of the present invention, the transformer is run at the optimal frequency and only as a power supply in order to produce the high voltage output and rectify it back to DC. Therefore, in this circuit a low-voltage battery has been transformed into a high-voltage battery which powers a high-voltage circuit, namely the transconductance amplifier 33 which puts out a constant current independent of load impedance. Because it has been shown that sensation is proportional to current and not to power, this type of constant current output prevents any problems concerning changing resistance of skin or electrode paste on neuron resting membrane potential. Therefore, in this machine nothing inherently limits the bandwidth within the circuit.

The 10 V supply 46 powers waveform generator 48. The frequency is set by 3 hand-switched capacitors 36' and the frequency control 34 potentiometer. Sine, sawtooth, and square wave outputs are provided but the present invention uses the sine wave output. Due to the different levels and output impedences of the outputs, compensating resistor networks 49 are included. The ±50 V supply 47 supplies power to high compliance transconductance amplifier 33. A ±15 V supply is provided by a zener regulated supply for operation of input amplifier 32 which drives transconductance output stage amplifier 33.

The load is driven in a floating configuration with the current sensed across at 100 Ohm resistor 51 which provides a 10 mA/V transfer function.

Sense resistor 51 is used since monitoring is done at the subject leads and not on the primary side of variable loss transformer 45.

Figure 7:
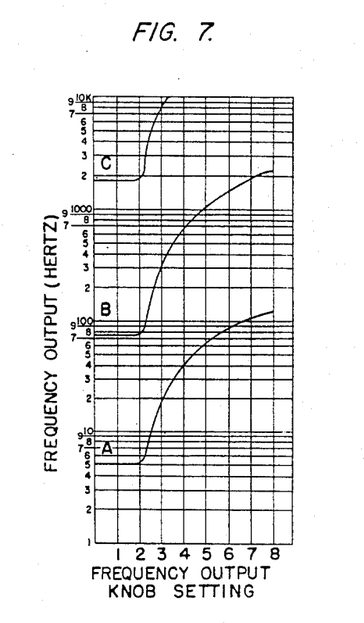
FIG. 7 is a graph showing frequency band outputs for knob settings of the electrical stimulator of FIG. 4.
Figure 8:
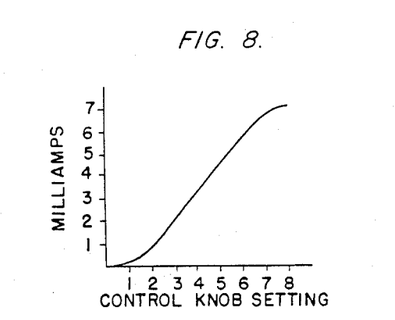
FIG. 8 is a graph of the current output level of the electrical stimulator of FIG. 4 with respect to amplitude control knob settings.

The setting for the frequency output on each of bands A, B, and C for the knob settings on frequency control 34 is shown on the graph of FIG. 7. The current output level for the knob settings on current output control 35 is shown on the graph of FIG. 8. These figures give a basis for frequency ranges and current levels used in the present invention.

An example of operation of apparatus of the present invention which demonstrates the frequency coded properties of human subjective psychological brain states as evoked by cutaneous electrical stimulation is as follows.

The subject should sit or lie down, relaxed, in a quiet room without any loud auditory or visual distractions. Dime electrodes 18 are placed approximately ¼ inch anterior to each earlobe with electrode paste placed between the skin and each electrode to serve as a conducting medium. The electrodes 18 may be held in a place by the use of standard athletic headband as shown. The current setting on the stimulator 12 is increased until a tingling sensation is felt at the electrodes. The initial frequency of stimulation may be randomly set.

Sufficient current must be emitted at the electrodes at all times so that a subjective nonadversive sensation which patients characterize as a slight tingling be felt at the electrodes. Any loss in the tingling sensation at the electrodes may require an adjustment of current intensity in order to continue to evoke the slight tingling sensation. The subjective sensation of cutaneous electrical stimulation is a function of the current, the frequency of the stimulation, both adjusted by electrical stimulator 12 (or signal generator 11), and the state of relaxation of the subject S.

In obtaining a profile of an individual subject adjustments of apparatus are made based on verbal feedback from the subject. The frequency output is adjusted to maintain the "slight tingling sensation" at electrodes 18. The subject reports any unusual auditory, visual, sensual vibration, or other sensation experienced. The subject may control stimulator 12 himself to effect various frequency sensitive subjective psychological states. Frequency outputs of stimulator 12 may also be adjusted without the subject's knowledge to collect further data.

Alternatively because of monitoring system 17 effects of the stimulation are obtainable even if the subject is unconscious and electrical stimulation can be applied without verbal feedback from the subject.

Figure 9:
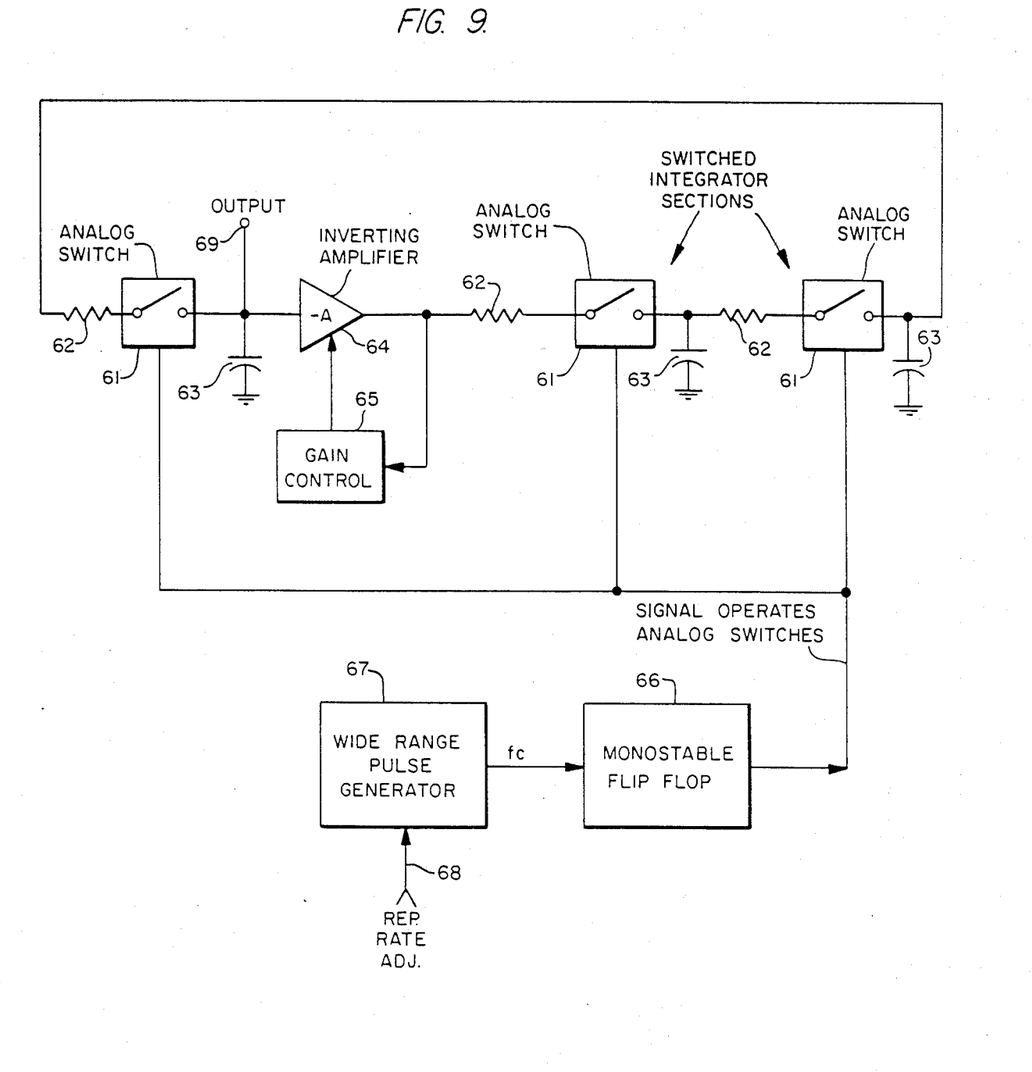
FIG. 9 is a block diagram of another embodiment of a sinusoidal oscillator used in place of the signal generator and a portion of the electrical stimulator of FIG. 5.

As stated previously, other signal generation means can be used with the present invention to produce a sinusoidal oscillation. Such an oscillator which has unique advantages of a very wide frequency range with a single control, low power, low distortion, stable low frequency performance without large value resistors and capacitors, and low cost is described in FIGS. 9 and 10. FIG. 9 shows the oscillator in block form while FIG. 10 shows the same oscillator with logic circuitry.

Figure 10:
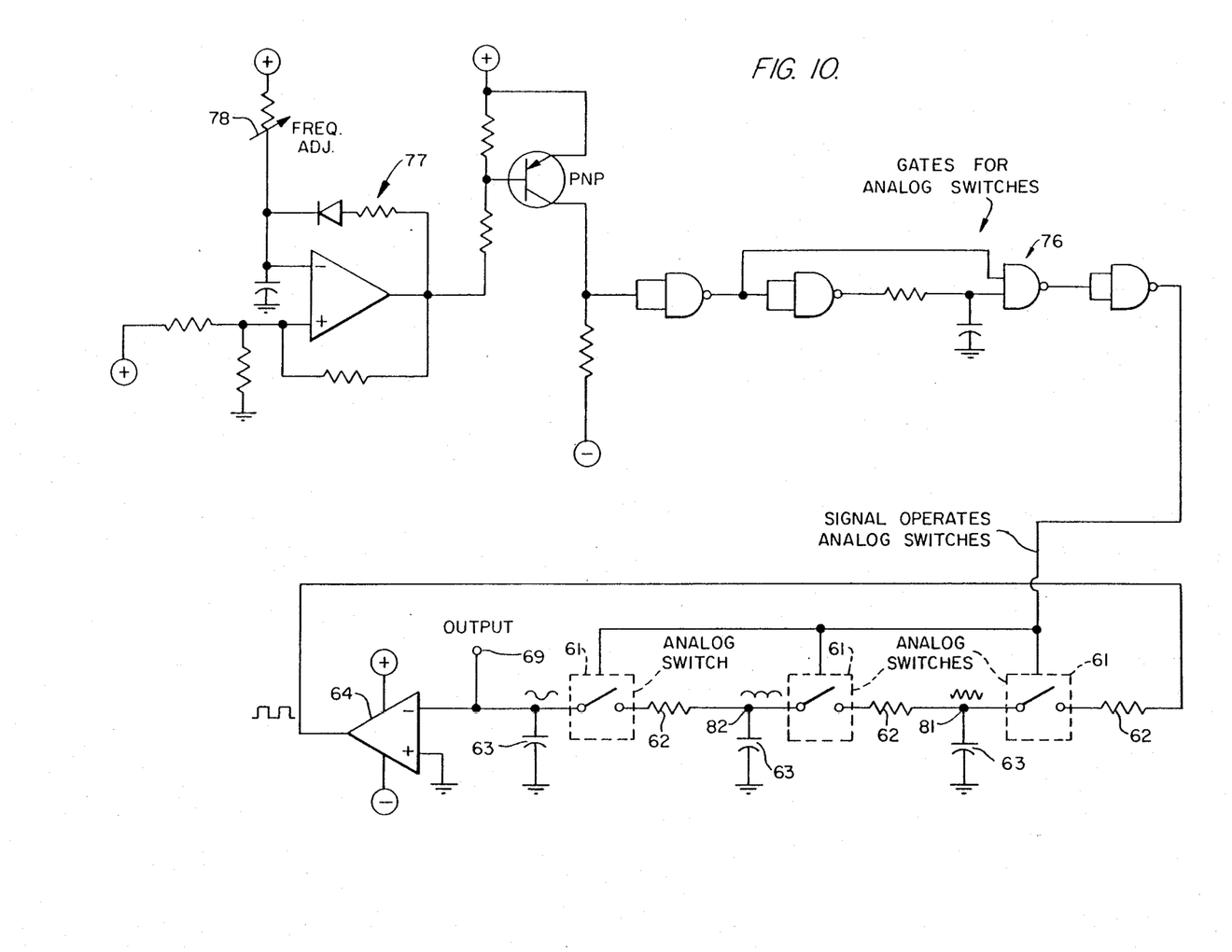
FIG. 10 is a more detailed illustration of circuitry of the embodiment of FIG. 9.

Such sinusoidal oscillator of FIGS. 9 and 10 would substitute in FIG. 5 for signal generator 11 and for waveform generator 48. Since only 4 to 6 volts is required to supply this substituted oscillator, the 10-volt supply 46 may be changed to a 4 to 6-volt supply. The oscillator would then be substituted with advantages enumerated above and following.

Prior design for sinusoidal oscillators of the R-C type (Wien Bridge, R-C phase shift, twin-tee) do not allow wide adjustment range with a single control. All of the standard RC sinusoidal oscillators require simultaneous adjustment of at least two controls to achieve even 10:1 range. The design of FIGS. 9 and 10 provides greater than 1000:1 range with a single control. Another common type of sinusoidal oscillator is the LC type, Both the RC and LC types share the disadvantages of limited adjustment range and are not practical at low frequencies. Prior design sinusoidal oscillators that can approach the wide adjustment range of the oscillator of the present invention are the clipped triangle wave function generators which have inherent poor distortion characteristics or the type that rely on heterodyne mixing of two high frequency sinusoids. This variety has very poor frequency stability at low output frequency. A new technique is shown in FIG. 9. Only three switched integrator sections, each having an analog switch 61, a resistor 62 and a capacitor 63 are shown. Three is the minimum number, although preferably more can be used which lowers the distortion from the amplifier 64 and the gain control 65. The amplifier 64 has an inverting minimum gain of $|1/(jw_oRC+1)|^n$ where $j \simeq \sqrt{-1}$, R=total of resistor and switch resistance, C=total of switch capacitance to ground and capacitor, n=number of stages, and $W_o$=the natural frequency of the oscillator where the switches are left on. Gain control 65 can be as simple as allowing the amplifier 64 to clip (saturate) or any of the more refined techniques known. The analog switches 61 are any of the many known analog switches in the field, such as, for example, Model CMOS 4016, which is manufactured by several companies such as RCA and Motorola Corporation. Likewise monostable, flip-flop 66 which has an output signal which operates analog switches 61 is any of the common monostable designs in the field. The pulse generator 67 may also be any common technique of producing a wide frequency range pulse output. Wide range pulse generator 67, through monostable flip-flop 66 supplies the signal at the adjusted repetition rate of adjustment 68 to operate analog switches 61 which control the output at 69 through amplifier 64.

The function of the circuit is simply understood if it is realized that the circuit functions as a normal RC phase shift oscillator when the switches are closed (much less time than a normal cycle of the oscillator would require) and that the circuit holds its output constant while the switches are open. Thus the output frequncy is at $f_o/D$ where $f_o$ is the natural frquency of the RC oscillator and D is the duty cycle of the signal during the time that the analog switches operate.

The use of a constant pulse width with repetition rate modulation adjustment places the switching frequency at a constant multiple of the output frequency (a fixed number of steps in the output wave-form). A constant repetition rate with a variable duty cycle could also be used which results in a constant switching frequency but this results in a variable number of steps in the output wave-form with the minimum number of steps at the maximum output frequency. This makes it more difficult to achieve a wide output frequency range when faced with minimum pulse width considerations. The form of the circuit used in such a device is shown in FIG. 2.

In FIG. 10 analog switches 61 are associated with their respective resistors 62 and capacitors 63 to form switched integrator sections with a signal from logic gates 76 operating analog switches 61. A form of wide range pulse generator circuit 77 with frequency adjustment 78 feeds the pulses at adjusted frequency to gates 76. Amplifier 64 in series with the switched integrator sections conducts the signal to output 69 from whence output is fed through the stimulator apparatus which connects with the subject.

For further experimental purposes, it is possible that a square wave or sawtooth wave, besides the sinusoidal wave, might be required. The oscillator of FIGS. 9 and 10 has this versatility as shown in FIG. 10 where a sawtooth output may be picked off at point 81 and a parabolic wave at point 82. A square wave output may be picked up from the output of amplifier 64. The sine wave output is picked off at output 69.

Within the range of the equipment of the present invention several distinct frequency sensitive subjective psychological states may be observed in the subject.

Between the frequency range of 5 and 19 hertz subjects reported that their visual field appeared to be pulsating or oscillating. This was not accompanied by any apparent movement of the eyeballs.

At the next higher frequency of stimulation, from 12 Hz to 80 Hz, subjects reported a flickering pale white light, usually in the periphery of their visual fields which got faster with increasing frequencies of stimulation and eventually disappeared at approximately 80 Hz.

At 60 Hz to 573 Hz frequencies, subjects reported the feeling of a unique sensation of a relaxing hum, buzz, or vibration resonating from deep within their heads. In most cases this sensation peaks at 70 Hz.

The above ranges of frequencies within which the distinct subjective psychological states were described, were evoked in healthy subjects by constant alternating current sinusoidal waveform electrical stimulation transcutaneously applied to the head area.

When this type of stimulation is similarly applied to unhealthy subjects, the profile obtained of the parameters of the stimulation for evoked sensations is markedly different from the profiles obtained from the healthy subjects.

For example a narcotic addict presented a profile of the current threshhold for the evocation of the cutaneous tingling sensation approximately four times greater than a healthy subject. The narcotic addicts tested only were able to report a resonance sensation with the sinusoidal waveform of stimulation without the flickering or oscillation of visual field perception that was reported by healthy subjects at corresponding frequencies. This profile of the addict is one example of the type of information that the medical practitioner can obtain by this diagnostic procedure.

In further studies of the diagnostic procedure for obtaining a subject's profile of the frequency verses threshhold current intensity for the subjective sensation of cutaneous electrical tingling at the electrode sites it was found that the tingling sensation only may be evoked by electrodes placed at any area of the body and is not limited to the head area (as is the case for the other sensations described). In addition, it was found that for this form of cutaneous tingling sensation diagnostic profile procedure the waveform of electrical stimulation is not necessarily limited to a sinusoid.

The described sensations may be evoked by using a biphasic square wave stimulus but in such case the resolution of narrow frequency bands for a particular sensation is not present. With the square wave, these sensations are reported to occur together over a broad range of frequencies. For example, the flickering light sensation as well as the resonance sensation are reported as occurring together in the frequencies where only a flickering sensation is reported alone when a sine waveform is used. Furthermore, when a pulsed waveform such a 0.2 μsec. biphasic pulse is used, neither a flickering sensation nor an oscillation of visual field sensation is reported. Instead, with this pulsed stimulus, there is the report of experiencing a resonance sensation over a broad range of frequencies. Thus, for purposes of the present invention, a sinusoidal waveform is used.

When more than one frequency is applied such as when using triple output signal generator 11 in the system, psychological states corresponding with the several frequencies or sum and different frequencies will be experienced.

The present invention is used to induce different psychological states but due to the apparatus of this invention such states can be reached more quickly and with less current, thus reducing the danger from such currents to the subject.

The present invention has numerous practical applications dependent on attainment of these psychological states and controlled maintaining of such a state.

The subject first performs an act or is subjected to evoked response system 15. Such evoked response could include listening to certain sounds, seeing certain pictures, stimulation of the skin, subjection to a particular environment, or taking of a drug, such as by an addict. The monitoring system 17 receives electrophysiological parameters monitored from the subject and feeds this information to computer 13. Using this information, the electrical parameters of stimulation by the signal generator electrical stimulator apparatus 10 to electrically mimic the effects of the evoked response system in the subject can be determined. Computer 13 can be connected to control stimulation apparatus 10 to vary in accordance with maintaining a particular state based on information being received from monitoring system 17.

An important aspect of such a system is that by cutaneous electrical stimulation to produce particular psychological states, the need of the original evoked response system may be then eliminated and the subject may then be subjected or brought to the desired psychological state without repeating of the evoked response system which system as originally applied to the subject, may have deleterious effects on the subject. One such case may be in respect to additive drugs where their effect on the body may be simulated by cutaneous electrical stimulation at the point where the electrodes 18 of the present invention are placed on the subject. Such electrical stimulation being possible of close control may help in overcoming withdrawal symptoms without the use of the deleterious drug. Concomitantly with the cutaneous electrical stimulation for attenuation of withdrawal symptoms the subject may self-administer nitrous oxide gas ($N_2O$) (or a similar type cognitive activator) at physiological concentrations of approximately 60% $N_2O$ and 40% oxygen where conscious awareness is maintained. Such self-administration of $N_2O$ is to facilitate the formation of neuronal connections and the consolidation of the memory of the experience and should lessen the time needed for withdrawal than use of cutaneous stimulation alone. This process will serve to permit the former drug addicts to have conscious awareness of their natural electro-cotical and electro chemical state which they had been artificially inducing with the drugs. By sensitizing these natural systems within the brain through the use of cutaneous electrical stimulation, this process will induce an antibuse type of physiological state in the event of further drug use. Since the effects of cutaneous electrical stimulation involve primarily regions of the brain involved with non-verbal conscious stages of awareness, this therapy should include psychotherapy to bring to the subject's conscious awareness, through verbal communication, the effects of the electrical stimulation being administered. This may be done by electronically inducing a hypnotic state of awareness in the subject at which time a trained psychotherapist can explain to the subject that future self-administration of the drug is not necessary. If the desire for the drug again should occur, this desire can be relieved by the electrical stimulator which would reduce the physiological craving for the drug as well as evoking a psychoelectrical stimulus which is associated with a psychological state in which the drug is unnecessary.

Other uses may be made of the apparatus of the present invention and the method of the present invention may be applied to obtain other therapeutic results.

The words "cutaneous" and "cutaneously" to be correctly interpreted as to where electrical stimulation may be applied in the present invention includes the application of electrical stimulation on surfaces of the body even where such surfaces may extend into orifices of the body.

It will be obvious to those skilled in the art that various changes may be made without departing from the scope of the invention and the invention is not to be considered limited to what is shown in the drawings and described in the specification.

What is claimed is:

1. A method of diagnostic and therapeutic treatment of a patient comprising the steps of
    applying a source of electrical stimulation to the patient,
    applying alternating constant current electrical stimulation from said source,
    controlling the current and frequency of the stimulation within current parameters and through a range of frequency parameters including low frequencies which initiate non-adversive sensations.
2. The method diagnostic and therapeutic treatment of claim 1, further characterized by
    said alternating constant current electrical stimulation being in the form of a continuous sine wave.
3. The method of diagnostic and therapeutic treatment of claim 1 or 2, further characterized by
    providing a unique individual profile or medical record of the frequency versus threshhold current intensity at which the patient feels the subjective sensation of electrical tingling where the electrical stimulation is applied to the patient.
4. The method of diagnostic and therapeutic treatment of claim 1 or 2, further charcterized by
    providing a unique individual profile or medical record of the frequency versus threshhold current intensity at which a monitoring means monitors the response evoked by the electrical stimulation applied to the patient.
5. The method of diagnostic and therapeutic treatment of claim 1 or 2, further characterized by
    providing a unique individual profile or medical record of the frequency versus current intensity at which the patient has a physiological state induced.
6. The method of diagnostic and therapeutic treatment of claim 1, further characterized by
    said source of electrical stimulation being applied at the head area of the patient.
7. The method of diagnostic and therapeutic treatment of claim 6, further characterized by the steps of
    controlling the frequency to a range within which the visual field of the patient appears to be pulsating or oscillating,
    controlling the frequency to a range within which the patient perceives a flickering pale white light,
    conrolling the frequency to a range within which the patient experiences a reasonance or vibratory sensation emanating from his head.
8. The method of diagnostic and therapeutic treatment of claim 7, further characterized by controlling the frequency to a range between 5 to 19 hertz within which range there appears to the patient to be the distinct sensation of a pulsating or oscillating visual field.

9. The method of diagnostic and therapeutic treatment of claim 7, further characterized by
controlling the frequency to a range between 12 to 80 hertz within which the patient perceives a distinct sensation of a flickering pale white light.

10. The method of diagnostic and therapeutic treatmen of claim 7, further characterized by
controlling the frequency to a range between 60 to 573 hertz within which the patient experiences a distinct resonating or vibratory sensation emanating from his head.

11. The method of diagnostic and therapeutic treatment of claim 7, 8, 9 or 10, further characterized by
providing a unique individual profile or medical record, varying with the patient's state of health, of a patient's electrophysiological state or sensations which are evoked in response to various parameters of electrical stimulation.

12. Bio-electric stimulation apparatus for diagnostic and therapeutic treatment of a patient comprising
a source of alternating constant current electrical stimulation
means to apply said source of electrical stimulation to the patient,
means to control and vary the current and frequency of the stimulation within current parameters and through a range of frequency parameters determined by subjective sensations experienced by the patient,
said source of alternating constant current electrical stimulation being capable of variation of frequency at least between 5 to 573 hertz.

13. The apparatus of claim 12, further characterized by
means for connection to the patient to obtain the bio-electrical characteristics of the patient at the current and frequency parameter which initiate the non-adversive sensation which is characterized as tingling.

14. The apparatus of claim 12, further characterized by
means for connected to the patient to obtain the bio-electrical characteristics at discrete frequency ranges within which the visual field of the patient appears to be pulsating or oscillating, within which the patient perceives a flickering pale white light, and within which the patient experiences a resonating or vibrating sensation emanating from his head.

15. The apparatus of claim 12, further characterized by
said control means including a single control to vary the frequency of said source over its range of frequency at least between 5 to 573 hertz.

16. The apparatus of claim 12, further characterized by
said source of alternating constant current electrical stimulation including
a sinusoidal oscillator of wide frequency range covering at least between 5 and 573 hertz.

17. Bio-electric stimulation apparatus for diagnostic and therapeutic treatment of a patient comprising
a source of alternating current electrical stimulation,
means to apply said source of electrical stimulation to the patient,
means to control the current and frequency of the stimulation within current parameters and through a range of frequency parameter including low frequencies determined by subjective sensations experienced by the patient,
means for connection to the patient to obtain the bio-electrical characteristics of the patient at the current and frequency parameters which initiate the non-adversive sensations.

18. The apparatus of claim 17, further characterized by
means to monitor the actual bio-electrical characteristics of the patient connected to said means to obtain such characteristics under predetermined conditions
and means to modify current and frequency connected to said control means and said monitor means to achieve bio-electrical characteristics in the patient related to the actual bio-electrical charcteristics monitored.

19. The apparatus of claim 18, further characterized by
the bio-electrical characteristics being the psycho-electro-physiological state of the patient.

20. The apparatus of claim 18, further characterized by
said modifying means including a computer means connected to said monitoring means and said source of electrical stimulation to receive information from said monitoring means as to the actual bio-electrical characteristics of the patient and to control said source of stimulation applied to the patient in accordance with the receipt of the information from said monitoring means.

21. The apparatus of claim 20, further characterized by
means to apply evoked response stimuli by psycho-physical interaction to the patient
said means to apply stimuli being connected to and responding to interaction with said computer means.

22. The apparatus of claim 17, further characterized by
said means to apply said source of electrical stimulation including
a pair of electrodes adapted for placement closely anterior of the earlobes of the patient.

23. The apparatus of claim 17, further characterized by
said source of electrical stimulation including
signal generator means having constant current means to maintain a constant current output to the patient at any setting of current amplitude and changes in circuit resistance in connection with the patient.

24. The apparatus of claim 23, further characterized by
said constant current means including a transconductance amplifier having an output to the patient.

25. The apparatus of claim 23, further characterized by
said means to apply said source of electrical stimulation including
a pair of electrodes adapted for placement on the patient,
said signal generator means including
a waveforming means, amplifier means connected in a signal path from said waveforming means to said constant current means, said amplifier means also being connected to one of said pair of electrodes and said constant current means being connected to the other of said pair of electrodes.

26. The apparatus of claim 25, further characterized by said signal generator means including a sensing resistor means to monitor the output to the patient connected to ground from a connection from said amplifier means and said electrode connected thereto.

27. The apparatus of claim 17, further characterized by said means for connection to the patient to obtain the bio-electrical characteristics of the patient having a range of operation to include ranges within which the visual field of the patient appears to be pulsating or oscillating, within which the patient perceives a flickering pale white light, and within which the patient experiences a resonating or vibrating sensation emanating from his head.

* * * * *